United States Patent [19]

Attar

[11] Patent Number: 4,840,919
[45] Date of Patent: Jun. 20, 1989

[54] GAS DOSIMETER FOR COLORIMETRICALLY INDICATING THE PRESENCE OF AMIDES

[75] Inventor: Amir J. Attar, Raleigh, N.C.

[73] Assignee: Perfect View, Inc., Raleigh, N.C.

[21] Appl. No.: 21,247

[22] Filed: Mar. 3, 1987

[51] Int. Cl.$^4$ ............................................. G01N 2/78
[52] U.S. Cl. ...................................... 436/111; 422/57; 422/87; 436/112
[58] Field of Search .................. 436/111, 112; 422/57, 422/86, 87

[56] References Cited

U.S. PATENT DOCUMENTS

| | | | |
|---|---|---|---|
| 3,681,027 | 8/1972 | Smith | 436/11 |
| 3,787,184 | 1/1974 | Novak et al. | 436/111 |
| 3,811,840 | 5/1974 | Bauer et al. | 436/111 |
| 3,992,153 | 11/1976 | Ferber et al. | 23/232 |
| 3,999,946 | 12/1976 | Patel et al. | |
| 4,063,452 | 12/1977 | Bradshaw | 73/73 |
| 4,144,067 | 3/1979 | Rickert et al. | 430/324 |
| 4,327,575 | 5/1982 | Locker | 73/23 |
| 4,348,358 | 9/1982 | McKee et al. | 422/56 |
| 4,495,291 | 1/1985 | Lawton | 436/1 |

OTHER PUBLICATIONS

K. Hartke and U. Lohmann, "Chem. Lett.", pp. 693–696, (5), 1983.
Grundmann, "Methoden der Org. Chem.", VII (36), Ed. by E. Muller and O. Bayer, pp. 106–108, 1979.
U. Lohmann et al., "Dfsch. Apoth.-Ztg.", 123 (21), pp. 1013–1021, abstract, 1983.
U. Lohmann et al., "Arch. Pharm.", 317 (4), pp. 313–323, 1984.
T. Bartos and M. Pesez, "Talanta", 19, pp. 93–124, 1972.
T. Bartos, "Talanta", 21 (12), pp. 1303–1304, 1974.
Dangwal et al., "Am. Ind. Hyg. Assoc. J.", 41 (11), pp. 847–850, 1980.

*Primary Examiner*—Barry S. Richman
*Assistant Examiner*—Timothy M. McMahon
*Attorney, Agent, or Firm*—Lynn E. Barber

[57] ABSTRACT

A gas dosimeter utilizing a colorimetric reagent for the selective determination of total amines in solution or in air is described. The reagent comprises 1,2 napthoquinone-4-sulfonic acid or a derivative thereof. Upon addition of amines, a color is formed which is quantitatively related to the number of amine molecules reacted. The reagent can be utilized to detect aromatic amines apart from primary amines by the addition of a buffering agent to maintain the pH less than 4.5.

5 Claims, 1 Drawing Sheet

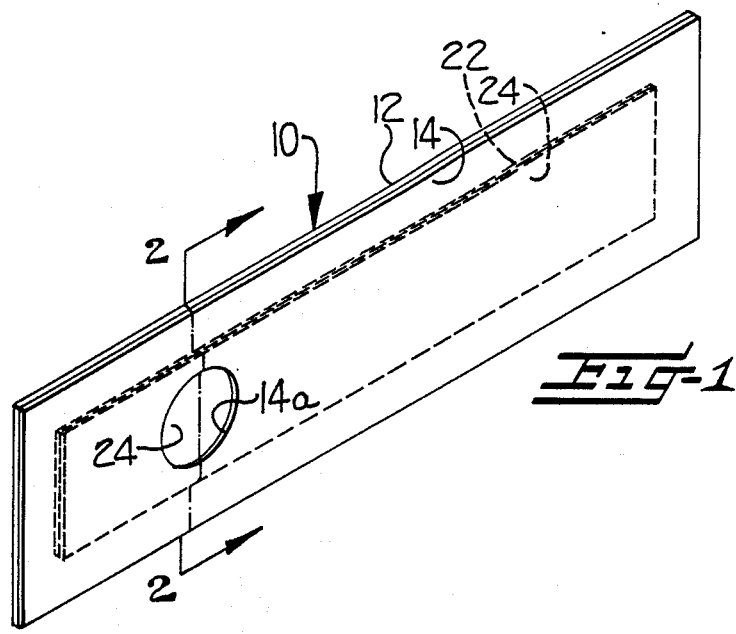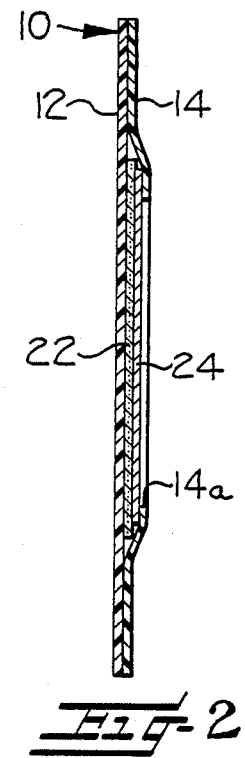

GAS DOSIMETER FOR COLORIMETRICALLY INDICATING THE PRESENCE OF AMIDES

FIELD AND BACKGROUND OF THE INVENTION

The present invention relates to a gas dosimeter for colorimetrically indicating the presence of total amines in solution or in air. Particularly, this invention relates to a gas dosimeter utilizing 1,2 naphthoquinone-4-sulfonic acid and derivatives thereof as the colorimetric reagent.

Aniline and other amines are an important class of chemicals which are widely used in various industries such as plastics, textiles, pharmaceuticals, dyes, etc. Because of increasing concern over safety and health hazards presented by exposure to amine vapors in air, industries require an effective and reliable way to monitor amine levels in the workplace environment and to detect exposure to potentially hazardous amine concentrations. Monitoring devices in the form of dosimeter badges have been developed for monitoring various toxic vapors such as formaldehyde, oxides of nitrogen, ethylene oxide, hydrogen sulfide and ammonia. Exemplary dosimeters are disclosed in U.S. Pat. Nos. 3,681,027 to Smith; 3,992,153 to Ferber et al; 4,063,452 to Bradshaw; 4,327,575 to Locker; 4,348,358 to McKee et al; and 4,495,291 to Lawton. However, currently there are no dosimeter badges available for monitoring exposure to amine vapors.

Typically, the measurement of amine vapors has required laboratory colorimetric analysis methods. Several reagents applicable in the laboratory for colorimetric determination of amines have been described in the literature. The basic method involves passing a known quantity of gas through an absorbing solution containing a colorimetric reagent and monitoring the change in color of the solution which is a function of the concentration of the amine in the absorbing solution. Several examples are described in Table 1 below.

TABLE 1
Published Colorimetric Reagents for the Determination of Amines In Solution

| Process or Reagent | Comments | References* |
|---|---|---|
| Diazotation | Specific to aromatic amines. The method is sensitive; however difficult to apply quantitatively. | 1–2 |
| Aromatic Substitutions | Very sensitive when fluorescence is used. Most common. Reagents are typically 2,4 dinitrochlorobenzene or naphthalene | 3–4 |
| Imines Formation With Aldehydes and Ketones | The aldehyde of choice is N,N—dimethylamino p-benzaldehyde. Red color is formed. Hydrazines interfere. | 4–5 |
| O—Quinones | Sensitive and selective. The reagent is unstable. | 6–7 |

*References
1. Seggia, S. and Hammer, J. G., "Quantitative Organic Analysis Via Functional Groups", 4th Ed., John Wiley and Sons, New York (1979).
2. Bordelin, F. J. and Kemp, C. R., Ind. Eng. Chemical Analysis, 18, 420 (1946).
3. Smilts, F. J. and Jones, E., "A Scheme of Qualitative Organic Analysis", London (1953).

TABLE 1-continued
Published Colorimetric Reagents for the Determination of Amines In Solution

| Process or Reagent | Comments | References* |
|---|---|---|
| 4. | Higuchi, T. and Bodin, J., "Pharmaceutical Analysis", T. Higuchi and E. H. Brochmann (Eds.), Wiley Interscience, New York (1951). | |
| 5. | Menzie, C., Anal. Chem., 28, 1321–22 (1956). | |
| 6. | Frame, E. G., Russell, J. A. and Whilhelm, A. J., J. Block, Chem. 255, 1949 (1943). | |
| 7. | Auerbach, M.E., "Drug Standards", 20, 165 (1952). | |

However, the above-noted known processes and colorimetric reagents all suffer from at least one of the following disadvantages:
1. They form color very slowly.
2. The reagents are unstable.
3. The reagents cannot be easily used in the field, namely they cannot be used in a dosimetry badge.
4. The reagents cannot be adapted to dry-chemistry application.
5. The reagents are non-selective to amines.

The present invention provides a colorimetric reagent useful in a gas dosimeter so that the presence of amines can be visually shown. Moreover, the reagent can be utilized to differentiate between total amines and aromatic amines through the use of a buffering solution. The availability of a colorimetric reagent which can visually show the presence of total amines or aromatic amines alone and which is adaptable for use in a gas dosimeter can help even unskilled personnel determine whether they are present in a dangerous environment.

SUMMARY OF THE INVENTION

The present invention is based upon a dry-chemistry colorimetric reaction involving 1,2 naphthoquinone-4-sulfonic acid ("NQSA") or a derivative thereof, on a thin wafer and amines. The reagent can be utilized in several forms such as alkali and alkaline earth metal salts, lower alkyl derivatives, nitro and halo derivatives and sulphonic acid derivatives. The alkali metal salts are the derivative of choice, with sodium and potassium salts being most preferred. The reagent is used with aliphatic or aromatic amines, and is particularly useful in monitoring aromatic or aliphatic primary amines.

The chemistry of the reaction proceeds via any one of three possible pathways:

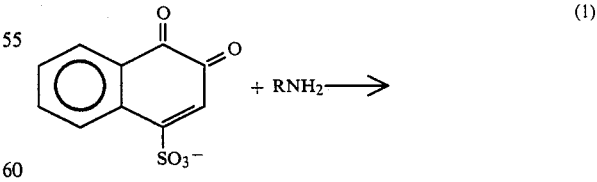

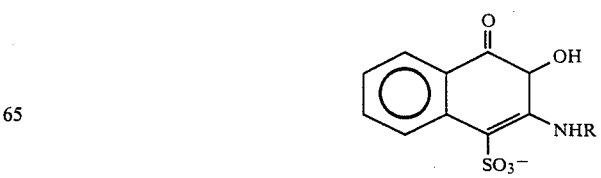

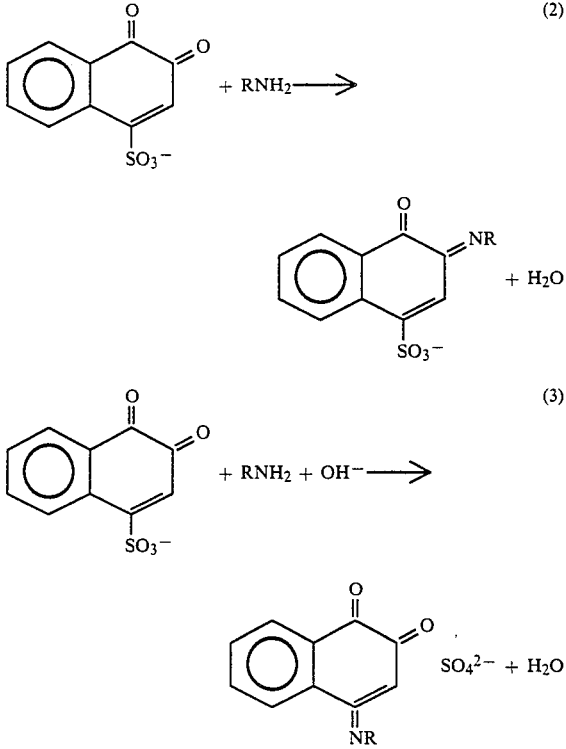

Additionally, the pH of the reagent may be adjusted by the addition of a buffering agent.

BRIEF DESCRIPTION OF THE DRAWINGS

FIG. 1 is a plan view of the top side of a gas dosimeter.

FIG. 2 is an enlarged sectional view taken along the line 2—2 in FIG. 1.

DETAILED DESCRIPTION OF THE INVENTION

The present invention now will be described more fully hereinafter with reference to the accompanying drawings, in which preferred embodiments of the invention are shown. This invention can, however, be embodied in many different forms and should not be construed as limited to the embodiments set forth herein; rather applicant provides these embodiments so that this disclosure will be thorough and complete, and will fully convey the scope of the invention to those skilled in the art.

The colorimetric reagent utilized in the present invention is 1,2 naphthoquinone-4-sulfonic acid or a derivative thereof. The reagent is typically used in the form of an alkali metal salt such as a sodium or potassium salt. Other suitable derivatives include alkaline earth metal salts, lower alkyl derivatives, nitro or halo derivatives and sulphonic acid derivatives.

Various additives may be included in the reagent in addition to the NQSA and buffer, such as for example, a stabilizer, an electrolyte, a solvating media, a gelling media, and polymers or prepolymers such as acrylate, polyvinyl alcohol, polyvinylidene ethylene oxide, polyethylene glycol, polyvinyl acetate and functionalized polystyrene.

The NQSA reagent can be employed to monitor aliphatic or aromatic amines, and is particularly useful in monitoring aromatic or aliphatic primary amines. The color formed with aromatic primary amines is red with a peak value in the range 520-560 nm. Exemplary aromatic primary amines include aniline, benzidine, napthyl amines and the like. The color formed with aliphatic primary amines is reddish brown with a peak value in the range 480-540 nm. Exemplary aliphatic primary amines include methylamine, butylamine and the like.

In addition to being useful as the chromophoric reagent in a gas dosimeter badge, the NQSA reagent may also be utilized in laboratory colorimetric methods for detecting and measuring amines.

The concentration of NQSA in the reagent is not critical, and may be varied over a wide range depending upon the sensitivity desired and the specific application. However, the higher the concentration, the more sensitive the reaction will be. With respect to pH, the reagent composition is preferably maintained at a pH greater than 5 for detecting total amines, and the pH may be adjusted if necessary by including in the reagent composition a suitable buffering compound, such as alkali metal phosphate, for example. If it is desired to determine the amount of aromatic amines apart from any aliphatic amines, the solution is buffered to a pH less than 4.5. A suitable way to achieve this buffering is via the addition of a phosphate salt and phosphoric acid. Typically, the stoichiometry of $NaH_2PO_4$ or $KH_2PO_4$ is adequate.

Referring now to the drawings, a gas dosimeter is shown therein in FIG. 1 and indicated generally by the numeral 10. The dosimeter 10 includes a base 12 and a cover 14. The base 12 comprises a generally flat, rectangular gas impermeable layer constructed preferably from a plastic material such as polyester, polyethylene, or the like. The base 12 may be comprised of a transparent plastic laminate formed by one or more layers of plastic material. For example, base 12 may comprise an outer plastic film of approximately 10 mils, laminated to a second plastic support layer of approximately 40 mils by a polyethylene adhesive.

Overlying the base 12 is a layer containing the NQSA reagent which changes color in response to exposure to amine vapors. Preferably, and as illustrated, the reagent is disposed on a carrier medium 22 by applying the reagent dropwise to the carrier medium and allowing the reagent to dry. The carrier medium may comprise a thin strip of paper or paper-like material, or a thin layer of a sorbent such as silica or alumina. In the preferred embodiment illustrated, the carrier medium comprises a thin paper-like strip in which there is dispersed a granular sorbent material such as silica or alumina. The sorbent functions to receive and carry the color-forming chemical which is utilized to indicate exposure to a specific gas.

As best seen in FIG. 2, the carrier medium 22 is of smaller lateral and longitudinal dimensions than the base 12 such that peripheral portions of the base project beyond the carrier medium 22. Overlying the carrier medium 22 and the reagent is a gas impermeable cover 14. As illustrated, the cover 14 is laminated to the case 12 along the peripheral edge portions so that the carrier medium 22 and the color-forming reagent carried thereby are totally encapsulated and sealed within the dosimeter 10. The cover 14 is formed of a gas impermeable plastic material, preferably a transparent plastic. As best seen in FIG. 1, an opening 14a is formed in the cover 14 to allow ambient air to enter the dosimeter and contact the reagent in the area located beneath the opening.

A porous membrane layer 24 is disposed over the carrier medium 22 and specifically over the portion of carrier medium which is under the opening 14a in the cover 14. The purpose of the membrane layer is to reduce errors caused by the effects of wind and moisture on the chromophore. The presence of a permeable membrane overlying the chromophore reduces the effect of the wind superfacial velocity.

It is to be noted that the reagent decomposes when exposed to UV light and should be protected from UV light and oxidation. Thus, the cover 14 and/or membrane layer 24 may be made of UV absorbing material so as to avoid exposing the reagent on the carrier medium to UV light.

EXAMPLE 1

An exemplary formulation of chromophoric reagent for the detection of traces of total amines in solution is to add 4 g of the sodium salt of NQSA to 20 g of water as a solvent for the mixture. The mixture is then warmed to 40° C. to solubilize the reagent. The mixture is then cooled and filtered.

EXAMPLE 2

An exemplary formulation of the buffered chromophoric reagent for the detection of only aromatic amines in air is the same formulation as Example 1, but with 1 g of $NaH_2PO_4$ added to maintain the pH of the solution at about 4.5.

EXAMPLE 3

The reagent of Example 2 is used in a dosimeter badge for detection of only aromatic amines by applying drops of the buffered reagent to the carrier media and allowing the reagent to dry. The chromophore-treated carrier is then encapsulated in a gas impermeable plastic material having an opening to allow the amine vapors to enter. Upon exposure to amine vapors, the chromophore-treated carrier changes color, forming a bright red color which is quantitatively related to the number of amine molecules reacted.

EXAMPLES 4 AND 5

A chromophoric reagent is produced with the formulation as set forth in Examples 1 and 2, but substituting the potassium salt of NQSA for the sodium salt of NQSA.

It will be seen that the invention provides a colorimetric reagent useful in a gas dosimeter which changes color in response to exposure to amines. Such a dosimeter greatly simplifies the dosimetry of hazardous vapors and provides an effective safety measure for monitoring exposure to amine vapors. Moreover, by the use of a buffered reagent with a pH below 4.5, aromatic amines can be monitored separate from total amines.

The foregoing embodiments are to be considered illustrative rather than restrictive of the invention, and those modifications which come within the meaning and range of equivalents of the claims are to be included therein.

That which I claim is:

1. A method for colorimetrically indicating the presence of aromatic amines which comprises exposing the aromatic amines to a chromophoric reagent comprising 1,2 naphthoquinone-4-sulfonic acid or a derivative of 1,2 naphthoquinone-4-sulfonic acid and an effective concentration of a buffering agent to maintain the pH of said reagent less than 4.5, and observing the change in color of said reagent.

2. In a gas dosimeter which includes a chromophoric reagent which changes color in response to exposure to specific vapors or gases, the improvement wherein the chromophoric reagent comprises 1,2 naphthoquinone-4-sulfonic acid or a derivative of 1,2 naphthoquinone-4-sulfonic acid and a buffering agent which maintains the chromophoric reagent at a pH less than 4.5.

3. A gas dosimeter according to claim 2 wherein said buffering agent is sodium dihydrogen phosphate.

4. A gas dosimeter according to claim 2 wherein said buffering agent is potassium dihydrogen phosphate.

5. A gas dosimeter for colorimetrically indicating the presence of aromatic amines, said dosimeter comprising a housing having means defining an opening therein through which ambient gas may pass, a carrier layer disposed within said housing, and a chromophoric reagent on said carrier which changes color upon exposure to aromatic amine vapors, said chromophoric reagent comprising 1,2 naphthoquinone-4-sulfonic acid or a derivative of 1,2 naphthoquinone-4-sulfonic acid and a buffering agent which maintains said chromophoric reagent at a pH less than 4.5.

* * * * *